United States Patent [19]

Petersen et al.

[11] Patent Number: 5,217,871
[45] Date of Patent: Jun. 8, 1993

[54] **MONOCLONAL ANTIBODIES TO *LEPTOSPHAERIA NODORUM***

[75] Inventors: Frank P. Petersen, Burlington, N.J.; Mark D. Clymer, Norristown, Pa.; Sally A. Miller, Pennsauken, N.J.; James H. Rittenburg, Perkasie, Pa.; G. David Grothaus, Burlington, N.J.

[73] Assignee: Ciba-Geigy Corporation, Ardsley, N.Y.

[21] Appl. No.: 570,495

[22] Filed: Aug. 21, 1990

[51] Int. Cl.$^5$ .................. G01N 33/569; C07K 15/28; C12N 5/00
[52] U.S. Cl. .................. 435/7.31; 435/7.92; 435/240.27; 435/975; 530/388.5; 530/389.1; 530/391.1; 530/391.3
[58] Field of Search .................. 435/7.31, 240.27, 911, 435/975; 436/547, 548, 518; 530/387, 823, 388.5, 391.1

[56] References Cited

U.S. PATENT DOCUMENTS

| | | | |
|---|---|---|---|
| 4,803,155 | 2/1989 | Petersen et al. | 435/7.31 |
| 4,845,197 | 7/1989 | Petersen et al. | 435/7.31 |
| 4,879,217 | 11/1989 | Petersen et al. | 435/7.31 |
| 5,037,755 | 8/1991 | Burr et al. | 435/210.27 |

FOREIGN PATENT DOCUMENTS 0234501 9/1987 European Pat. Off. .
0292719 11/1988 European Pat. Off. .

OTHER PUBLICATIONS

Nameth et al, Phytopathology, vol. 80, No. 11: pp. 1208-1211 (1990).
American Type Culture Collection Catalogue of Strains I, 15th Ed. 1982 p. 500.
Maurer et al "Proteins and Polypeptides as Antigens" in Methods of Enzymology, vol. 70 pp. 49-69 (1980).
Farr et al., 1989, Fungi On Plants and Plant Products in the United States, APS Press, St. Paul., Minn., pp. 799-807.
Kohler et al., 1975, Nature 256:495-497.
Littlefield, 1964, Science 14:709-710.

*Primary Examiner*—Esther L. Kepplinger
*Assistant Examiner*—Carol E. Bidwell
*Attorney, Agent, or Firm*—Shawn P. Foley

[57] ABSTRACT

The invention relates to monoclonal antibodies that react specifically with members of the genus Leptosphaeria and hybridomas that produce such antibodies. The invention is further directed to a method for making a hybridoma cell line that produces monoclonal antibodies that react specifically with Leptosphaeria nodorum, and a method of obtaining monoclonal antibodies therefrom. Methods and kits for diagnosing Leptosphaeria infections in plant material using such monoclonal antibodies are also within the scope of the invention.

7 Claims, 1 Drawing Sheet

FIG. 1

MONOCLONAL ANTIBODIES TO *LEPTOSPHAERIA NODORUM*

1. FIELD OF THE INVENTION

The present invention relates to the field of diagnostic plant pathology. More specifically, the invention relates to monoclonal antibodies useful in the detection of species of the pathogenic fungal genus Leptosphaeria. More specifically, the present invention provides monoclonal antibodies which react specifically with a single species of Leptosphaeria.

2. BACKGROUND OF THE INVENTION

2.1. FUNGAL PATHOGENS

Fungi as a group cause many plant diseases. For purposes of discussion the fungi can be classified as belonging to one of three major taxonomic classes: Basidiomycetes, Phycomycetes, or Ascomycetes.

Basidiomycetes

Members of this class are identified by the presence of a sexual-spore forming structure known as a basidium. Pathogenic forms include smuts, rusts and fleshy species such as mushrooms. Examples include wheat rust, white pine blister rust, cedar-apple rust, and smuts causing disease in corn, oats, barley, onions and wheat.

Phycomycetes

Members of this class are considered to be more primitive than members of either the Ascomycetes or Basidiomycetes, their distinguishing morphological feature being the absence of mycelial crosswalls. Examples of disease caused by members of the class include the downy mildews of grape and other hosts, root rot and late blight of potato and tomato.

Ascomycetes

Members of this class possess a specialized reproductive structure (an ascus) in which meioss and sexual spore formation take place. Examples of the more common plant diseases in which Ascomycetes have been identified as the etiologic agent include: powdery mildews on cereals, fruits and many other crops; Dutch elm disease; ergot of grains; peach and plum brown rot; black spot of roses as well as apple scab.

2.2. LEPTOSPHAERIA PATHOGENS

With respect to the present invention, members of the class Ascomycetes and the family Pleosporaceae, and particularly the genus Leptosphaeria, are of particular interest. The genus is a large one, containing many species that are plant pathogens of great economic importance. A recent compilation of plant pathogenic fungi in the U.S. lists 140 species of Leptosphaeria as plant pathogens (Farr, D. F., Bills, G. F., Chamuris, G. P. & Rossman, A., 1989, *Fungi on Plant and Plant Products in the United States*, APS Press, Minneapolis). The fruiting body of Leptosphaeria is an ostiolate, perithecioid pseudothecium containing bitunicate asci, each containing eight ascospores with three or more septations. In many cases, the ascospores are the primary mechanism of survival of pathogenic Leptosphaeria species in the absence of a susceptible host plant or under unfavorable environmental conditions. Ascospores often also serve as the primary source of inoculum in a host crop. Many of the species of Leptosphaeria also produce non-sexual, conidial stages; conidia may be borne in pycnidia, in acervuli, or on free conidiophores. In many instances, the conidial stage is most often found in nature. The conidial stage is usually classified separately from the sexual stage on the basis of morphology. Thus, species in the genus Leptosphaeria have conidial stages classified as a number of different genera of Imperfect Fungi (Deuteromycetes).

The system of classification of asexual stages of ascomycetous fungi is generally considered to be artificial but continues for practical reasons, since the sexual stages are often difficult to find in nature and may be difficult to induce in pure culture. However, the degree of relatedness of species to one another is reflected in the sexual classification; i.e. two species of Leptosphaeria are likely to be more closely related genetically to one another than two species of Septoria, which are named on the basis of morphological similarities of the asexual stage.

Pathogenic species of Leptosphaeria cause disease on above-ground parts of plants, most often the leaves and stems. Symptoms are lesions that may encompass a large portion of leaf area in irregular or regular patterns, depending on the crop. A number of severe and economically damaging diseases worldwide are caused by Leptosphaeria species, and require the use of resistant varieties and/or fungicides for control. *Leptosphaeria nodorum*, more commonly known by its asexual stage, *Septoria nodorum*, causes significant yield losses in wheat worldwide unless controlled by fungicides or resistant varieties.

*Leptosphaeria nodorum* exhibits a latent period of several weeks after infection, in which the pathogen grows in the tissue but symptoms of the disease (leaf and glume blotch) are not produced. Fungicides are most effective in controlling the disease if applied during the latent period, before significant damage occurs and secondary inocula are produced that will allow the disease to spread. However, routine preventative fungicidal treatments are not usually economically or environmentally justified, and a system that would permit very early detection of this pathogen, preferably during the latent phase of disease development, would be very useful in assuring that fungicides are used appropriately and provide maximal economic benefit. The present invention enables just such a system to be put into practice by providing monoclonal antibodies that are capable of detecting the presence of *Leptosphaeria nodorum* antigens, thus allowing early diagnosis of the disease, and possible prevention of widespread losses to wheat crops.

2.3. MONOCLONAL ANTIBODY TECHNOLOGY

Monoclonal antibodies can be prepared by any technique that provides for the production of antibody molecules by continuous cell lines in culture. These include the hybridoma technique originally developed by Kohler and Milstein (1980, Sci. Amer. 243(4): 66–74), the human B-cell hybridoma technique (Kozbor et al., 1983, Immunology Today 4: 72) and the EBV-hybridoma technique to produce human monoclonal antibodies (Cole et al., 1985, Monoclonal Antibodies and Cancer Therapy, Alan R. Liss, Inc., pp. 77–96). Each cell line synthesizes a homogeneous immunoglobulin that represents but one of the myriad of types of antibodies that an animal can synthesize in response to an antigen in vivo. Since each immunoglobulin-producing clone is characterized by the single type of antibody it produces, the term monoclonal antibody has been adopted. The advantages of monoclonal antibodies are numerous; they can be obtained in large supply; the preparation is homogeneous with respect to antigen reactivity and remains so over time.

The principle of hybridoma/monoclonal technology is predicated on the observation that when two somatic cells are fused, the resultant hybrid displays characteristics of both of the parent cell types. In the case of monoclonal antibody production, the ability to synthesize the particular antibody is derived from an immunocompetent cell (usually a spleen cell) taken from an immunized donor animal, whereas the ability to continuously divide in cell culture is contributed by the other fusion partner, a tumor cell line (often a myeloma). Early fusions were complicated by the fact that the myeloma cell line also produced a monoclonal antibody; thus the hybrid often produced two types of monoclonal antibody, one of myeloma origin and the other directed by the genetic information of the immunocompetent cell. Subsequently, tumor cell lines incapable of producing their own monoclonal have been used, e.g., SP2/0-Ag14 or X63-Ag8.653, thereby simplifying the analysis of the resultant fusion products.

Another technical consideration involves the rationale for selecting the successful fusion events (hybrid cells) from the two types of parental cells. Routinely a million or more cells of each type are used in the fusion protocol, and since fusion does not occur with 100% frequency, the job of trying to recover fusion products from the high background of unfused or self-fused parents can be formidable. As mentioned, hybridomas are formed by the fusion of short-lived antibody producing (spleen) cells and long-lived myeloma cells. The desired result is a long-lived cell line which produces antibody. Since the spleen cells have a finite life span in culture, one can simply wait an appropriate period for all the nonfused or self-fused spleen cells to die; however one must still recover from the resultant population the long-lived antibody producing cells from the long-lived antibody non-producing cells. A popular means for selection hybrid cells is the so-called HAT-selection system. This system involves the use of the enzyme hypoxanthine-guanine-phosphoribosyl transferase (HGPRT). This enzyme functions in the purine salvage pathway in mammalian cells. These cells are also capable of synthesizing purines de novo. Under most conditions, both pathways probably operate to a certain extent. If a cell lacks HGPRT, the salvage pathway is blocked and purines must be manufactured from non-purine materials.

The chemical 8-azaguanine is an antimetabolite which is capable of masquerading as the purine guanine and replacing it in some of its normal reactions. Azaguanine is incorporated into DNA, interfering with the normal growth pattern and leading to cell death. Since azaguanine must be salvaged, any cell which lacks HGPRT activity cannot utilize azaguanine and will grow in its presence.

A selective system which operates using the same enzyme but in the opposite sense in that HGPRT positive cells are selected is described by J. W. Littlefield (Science, 145:709 (1964)). It is called HAT and contains hypoxanthine, aminopterin and thymidine (HAT medium). Aminopterin is an antimetabolite that prevents de novo purine synthesis and methylation of deoxyuridylate to form thymidylate. Hypoxanthine can serve as a salvagable purine in the event that aminopterin blocks de novo purine biosynthesis while thymidine bypasses the necessity for the methylation of thymidylate. Thus, in the presence of aminopterin, any cell with positive HGPRT activity will proliferate while cells with negative HGPRT activity will die.

An alternate to the HAT system is the use of HMT medium in place of HAT. HMT employs amethopterin (methotrexate) in place of aminopterin. This method operates on the same principles, but the HMT medium is somewhat less toxic to the growing hybridomas, and therefore the cells can be left on the medium for a longer period of time.

In the hybrid system used for selection in accordance with the present examples, the myeloma cells are resistant to azaguanine and susceptible to aminopterin, that is, they are HGPRT negative. Thus, they will die in the presence of aminopterin. The antibody producing cells are HGPRT positive. By fusing the cells and growing them in HAT medium without azaguanine (HT medium), the successfully fused cells are selected because the myeloma cells which constitute the proliferating line can only grow where HGPRT activity is present and this activity must be supplied by the HGPRT positive cell line. The antibody producing HGPRT positive cell line are not killed in this medium. They will live for a time but will not proliferate.

Thus, by fusing the cells in a HAT or HMT medium, systems are produced in which the myeloma cells and antibody producing cells can grow long enough to produce hybrid cells but in which only the hybrid cells can survive and proliferate. After selection each hybridoma clone is then screened for the ability to produce the particular antibody of interest.

3. SUMMARY OF THE INVENTION

The present invention provides hybridoma cell lines that produce monoclonal antibodies that react specifically with at least one species of the genus Leptosphaeria, but do not react with species outside the genus. In one embodiment, the monoclonal antibody reacts specifically with a single species of Leptosphaeria. In a preferred embodiment, the antibody reacts specifically with Leptosphaeria (*Septoria*) nodorum. Throughout the specification, the name Leptosphaeria will be used interchangeably with the name of its anamorph or asexual stage; thus, an antibody which reacts with *Leptosphaeria nodorum* also reacts with the asexual stage *Septoria nodorum.*

The availability of these monoclonals provides a means for diagnosing Leptosphaeria infections in plant material. Thus, a method for diagnosing such infections is provided which comprises contacting a plant sample suspected of containing antigens of the pathogen of interest with an antibody having specificity for the pathogen, and observing the presence or absence of a reaction between the antibody and antigen present in the sample. In a preferred embodiment, the assay is conducted as a sandwich, or double antibody assay: a first antibody that reacts with the pathogen of interest is contacted with the plant sample, and then a second antibody which also reacts with the pathogen of interest is added, to form an antibody-antigen-antibody complex, if the antigen is present in the sample.

Also provided in this regard are kits for detection of Leptosphaeria which comprise an antibody, preferably immobilized, which reacts with the species of interest, and a detectably labeled antibody which reacts with the species of interest. At least one of the antibodies should be a monoclonal antibody of the present invention.

5. DETAILED DESCRIPTION OF THE INVENTION

Figure 1:
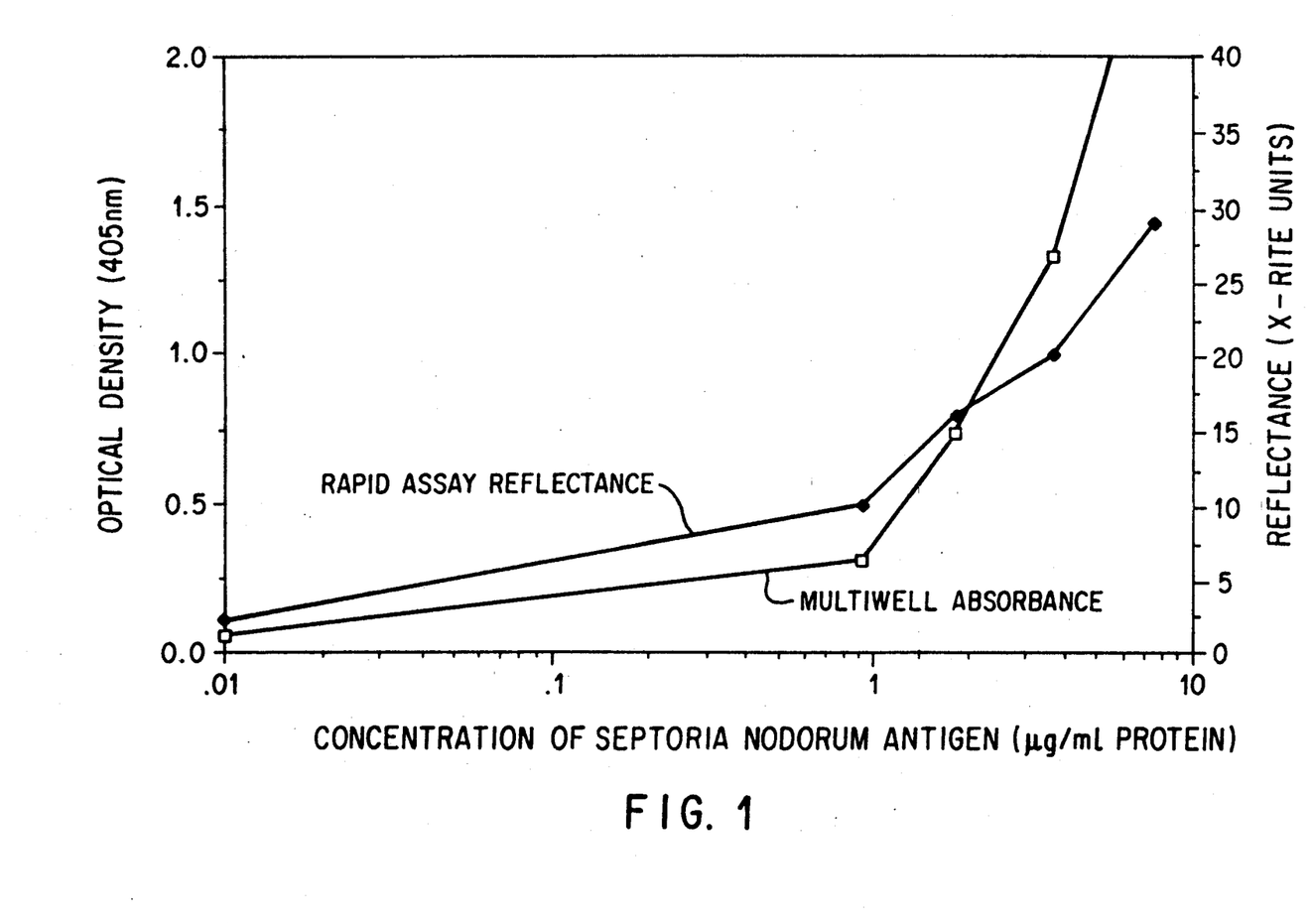
FIG. 1 shows a comparison of rapid and multiwell assay sensitivities to dilutions of Senl (004) in healthy wheat extracts.

5.Hybridoma Preparation 5.1.1. Leptosphaeria Extract Preparation

Leptosphaeria extract which contains antigen used in the production of monoclonal antibodies to Leptosphaeria may be prepared from a culture of Leptosphaeria. Leptosphaeria may be cultured on an agar solidified culture medium and/or in liquid culture medium examples of which include but are not limited to Czapek Dox V-8, Yeast malt, Potato Dextrose, Oatmeal. In a preferred embodiment, Czapek Dox is preferred (see Eyal et al., 1987, *The Septoria Diseases of Wheat Concepts and Methods or Disease Management*, Mexico:CIMMYT). The cultures may be harvested using standard procedures.

Extracts from the harvested Leptosphaeria fungi may be prepared using procedures known in the art. In a specific embodiment as will be described in Section 5.1., infra, extracts Leptosphaeria may be obtained by procedures known in the art such as processing the harvested Leptosphaeria through a Dyno-mill, or a Waring Blender, or through sonication, homogenization or shearing.

5.1.2. Immunization

The program for inoculation is not critical and may be any normally used for this purpose in the art. Such procedures are described, for example, in Goding, *Monoclonal Antibodies: Principles and Practice*, Academic Press, New York, 1983.

A useful program is one in which a first immunization is given intraperitoneally, of the antigen combined with an appropriate adjuvant. Booster injections can then be administered at two week intervals. Two or more boosters may be given. The animals are tail bled to determine if the serum contains antibodies specific to the antigen of interest. The animal is subsequently sacrificed and the spleen is removed to provide a source of lymphocytes.

5.1.3. Fusion

Fusion procedures for creation of hybridomas are well known in the art, and any of the known procedures are useful for the production of hybridomas producing Leptosphaeria-specific monoclonals. The basic procedure used in the present examples is a modification of that developed by Kohler and Milstein (*Nature* 256:495, 1975) and Hammerling (*Eur. J. Immunol.* 7:743, 1977). Other techniques which have recently become available, such as the human B-cell hybridoma technique (Kozbor et al., 1983, Immunology Today 4:72) and the EBV-hybridoma technique (Cole et al., 1985, Monoclonal Antibodies and Cancer Therapy, Alan R. Liss, Inc., pp. 77-96) may be used to produce human monoclonal antibodies are within the scope of the present invention.

In one embodiment, spleen cells (or alternately, peripheral blood lymphocytes) are isolated from the immunized animal, and the number of cells counted. T cells may be used as a feeder layer at a conoentration of 10 million cells/10 ml of medium. An appropriate immortal cell line, preferably a myeloma cell line is selected and added to the lymphocytes in a ratio of about 4:1 lymphocytes:myeloma. One useful myeloma cell line is the NSI cell line. At room temperature, PEG (polyethylene glycol) 1500 is added to the combined cells, and then diluted slowly with DMEM. After centrifugation, prewarmed HAT medium is added to the pellet which is resuspended. The sample is further diluted with HAT medium and small samples distributed to the wells of a microtiter plate. The plates are then placed in a 9% $CO_2$ incubation with at least 95% humidity. Cells are refed with HAT medium after 5-7 days. Clusters of hybridoma cells begin to appear after about 5-7 days. Further feedings are made with HT medium.

In one embodiment, pathogen extracts may be used. In a specific embodiment, material from a plant infected with the fungus may be used in a double antibody assay. Such a double antibody assay may involve the use of a polyclonal antibody made to Leptosphaeria as a capture antibody, the plant material, a monoclonal antibody supernatant, and anti-mouse-enzyme conjugate.

5.1.4. Screening

Those hybridomas producing antibodies to Leptosphaeria are identified using prepared fungal material of the particular species of interest in an ELISA format. In one embodiment, pathogen extracts may be used. In a specific embodiment, material from a plant infected with the fungus may be used in a double antibody assay. Such a double antibody assay may involve the use of a polyclonal antibody made to Leptosphaeria as a capture antibody, the plant material, a monoclonal antibody supernatant, and anti-mouse-enzyme conjugate. Those wells demonstrating positive responses in the ELISA are subcloned to select pure strains of hybridoma cells. The subcloned lines are retested for specific antibody activity to fungal components.

In order to determine the degree of specificity of the selected antibodies, it is desirable to further screen them against a panel of fungal pathogens which may be either related or unrelated to the Leptosphaeria. For example, to obtain a *Leptosphaeria* (*Septoria*) *nodorum*-specific antibody, the selected antibodies should be tested against other species of Leptosphaeria, as well as against more distantly related or unrelated species.

Examples of panels useful for the present purposes are presented in Tables 1 and 3. It is generally recommended to perform screenings in both a single and a double antibody format, as certain antibodies may be useful in one format, but not another.

5.1.5. Characterization of Antibodies

A number of antibodies falling within the scope of one or more of the claims of the invention have been produced according to the methods described. In one embodiment, a number of monoclonal antibodies have been produced which react specifically with *Leptosphaeria* (*Septoria*) *nodorum*. In a specific embodiment, the antibody is Sen15C6, an antibody of high specificity which may be used in a double antibody format. Sen15C6 is also strongly reactive with *Leptosphaeria nodorum*. The sole exception is an observed positive reaction with the "species" *Septoria avenae* f. sp. *triticea*. This nominal species is virtually identical morphologically to *Leptosphaeria* (*Septoria*) *nodorum* and causes similar symptoms on infected wheat. Thus, it is believed these two species are the same. Therefore, the antibody produced by hybridoma Sen15C6 is quite useful in the accurate and specific identification of *Leptosphaeria nodorum* antigens. This monoclonal is of the IgG2a immunoglobular subclass; however, other similar antibodies of other immunoglobular subclasses have also been prepared. The hybridoma Sen15C6 has been deposited with the American Type Culture Collection as accession number HB 10185.

Although hybridomas and monoclonals which identify *Leptosphaeria nodorum* represent a preferred embodiment, the present invention is not so limited. Utilizing the immunization fusion and selection methods described, supra, species specific monoclonal antibodies can also be made, using the appropriate species, extract as immunogen. For example, monoclonals having specificity for the species *Leptosphaeria korrae, L. maculans, L. pratensis, L. sacchari* are also within the scope of the invention.

5.2. Diagnostic Method and Kit

As shown above, the pathogens in question are capable of causing serious damage to those plants that are infected by them, and early diagnosis is therefore highly desirable. The present antibodies now provide a method by which the pathogens can be detected in plant material before any visible symptoms of the disease appear on the plant.

The antibodies described above may be used as the basic reagents of a number of different immunoassays to determine the presence of a particular species in plant material. Generally speaking, the antibodies can be employed in any type of immunoassay, whether qualitative or quantitative. This includes both single site and two-site, or sandwich, assays of the non-competitive type, as well as in traditional competitive binding assays. The antibodies may also be used in an on-site assay format, for example, using the immunoassay flow through device, disclosed in U.S. patent application Ser. No. 220,713 as incorporated by reference herein or the methods described in Section 6.5., infra.

Particularly preferred, for ease of detection, and its quantitative nature, is the sandwich or double antibody assay, of which a number of variations exist, all of which are intended to be encompassed by the present invention.

For example, in a typical forward assay, unlabeled antibody is immobilized on a solid substrate and the sample to be tested brought into contact with the bound molecule after a suitable period of incubation, for a period of time sufficient to allow formation of an antibody-antigen binary complex. Unbound material is then washed away. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique.

For the immunoassays of the present invention, the only limiting factor is that at least one antibody has the required specificity. Thus, a number of possible combinations are possible. For example, one antibody may be polyclonal, and the other monoclonal. Alternately, one antibody may be a general antibody, which binds both the pathogen of interest and other fungi, while the second antibody is specific for the pathogen of interest. Also, both antibodies may be specific for the pathogen of interest.

As a more specific example, in a typical forward sandwich assay, a general Leptosphaeria-binding antibody is either covalently or passively bound to a solid surface. The solid surface is usually glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art. Following binding, the solid phase-antibody complex is washed in preparation for the test sample. An aliquot of the plant extract to be tested is then added to the solid phase complex and incubated at 25.C, for a period of time sufficient to allow binding of any Leptosphaeria present to the antibody. The incubation period will vary, but will generally be in the range of about 2 minutes–16 hours. Following the incubation period, the antibody-Leptosphaeria solid phase is washed and dried, incubated with a second antibody specific for Leptosphaeria. The second antibody is linked to a reporter molecule, the visible signal of which is used to indicate the binding of the second antibody to any antigen in the sample. The term "reporter molecule", as used herein means a molecule which by its chemical nature, provides an analytically detectable signal which allows the detection of antigen-bound antibody. Detection must be at least relatively quantifiable, to allow determination of the amount of antigen in the sample. This may be calculated in absolute terms, or may be done in comparison with a standard (or series of standards) containing a known normal level of antigen.

The most commonly used reporter molecules in this type of assay are either enzymes, fluorophores or radionuclide-containing molecules. In the case of an enzyme immunoassay, an enzyme is conjugated to the second antibody, sometimes by means of glutaraldehyde or periodate. As will be readily recognized, however, a wide variety of different ligation techniques exist, which are well-known to the skilled artisan. Commonly used enzymes include horseradish peroxidase, glucose oxidase, $\beta$-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antigen-specific antibody is added to the first antibody-Leptosphaeria complex, allowed to bind to the complex, then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in the EIA, the fluorescent labeled PLF-specific antibody is allowed to bind to the first antibody-ferritin complex. After washing of the unbound reagent, the remaining ternary complex is then exposed to light of the appropriate wavelength, and the fluorescence observed indicates the presence of interest. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

6. EXAMPLES

The following examples illustrate the methods of preparation of the hybridomas and antibodies of the present invention.

6.1. Antigen Preparation

An agar plug from a viable culture of Leptosphaeria (Septoria) nodorum was inverted onto a C-D (Czapek-Dox) agar: (Difco) or PDA (Potato Dextrose Agar) (Difco) plate, and the plug was smeared over the surface. The plate was incubated at an ambient temperature and light for 5-7 days.

All of the colonies were aseptically removed from the agar plate and placed in a sterile 250 ml Omni-Mixer chamber. 50 ml of sterile Czapek's medium (Difco) was added to the Omni-Mixer chamber and the fungi were homogenized at 6000 rpm for 30 seconds.

Ten 250 ml Erhlenmeyer flasks containing 50 ml of Czapek's solution were inoculated with one ml of culture homogenate each. The inoculated flasks were placed on a shaker (high speed at 22°-24° C. with ambient light. After 13 days, the cultures were harvested and washed twice with PBS.

Fungal cultures were transferred into a 150 ml batch chamber of a DYNO-MILL type KDL containing 240 ml of 0.50 mm/lead-free glass beads [IMPANDEX]. The cooling jacket of the Batch chamber was precooled to 8.C with cold tap water. Extract was ground at 3000 rpm for 5 minutes after which the contents of the batch chamber were transferred to 50 ml centrifuge tubes and centrifuged at 13,000 rpm in a Sorvall RC-5B refrigerated centrifuge in an SS-34 rotor. The fungal supernatant was aliquoted and frozen until use. Total protein content of samples was in the range of 0.1-1.0 mg protein/ml.

6.2. Immunization and Fusion

A Balb/c mouse was immunized intraperitoneally with 0.2 ml fungal extract of isolate Sen 1-001 in 0.2 ml of Freund's complete adjuvant. The mouse was boosted 14 days later with the same fungal extract in Freund's incomplete adjuvant. A second boost followed in 12 days. The mouse was tail-bled 7 days later, and the serum tested for the presence of antibodies specific to the immunogen. The mouse was sacrificed by cervical dislocation the next day, and the spleen excised for extraction of lymphocytes. The spleen was placed on an 80-mesh sterile screen in a sterile disposable petri dish, cut with a scalpel and massaged with a sterile plunger from a 3 cc syringe. During this procedure, the spleen was rinsed several times with DMEM. The cell suspension was transferred to a sterile 50 ml disposable centrifuge tube. The screen and remaining tissue fragments were washed again with DMEM and the washings added to the tube. The cell suspension was spun down at 2000 rpm for 10 minutes (centrifugations were all at room temperature). The supernatant was decanted and the pellet washed with 4 ml of red blood cell lysing solution (0.83% $NH_4Cl$, 0.01 M $KHCO_3$, 0.1 mM EDTA) for 90 seconds at room temperature. The lysing reaction was halted by diluting the contents of the tube to 45 ml with DMEM. The contents were centrifuged again at 2000 rpm for 10 minutes. The supernatant was decanted and the pellet was resuspended in 10 ml DMEM. A sample of the cell suspension was retained for cell counting. The total number of viable cells in the suspension was $2.26\times10^8$ cells.

Myeloma cells (P3NSl/1-Ag4-1 (NSl) obtained from American Type Culture Collection, ATCC #TIB-18) were removed from culture medium by centrifugation in a 50 ml sterile centrifuge tube at 2000 rpm for 10 minutes. The supernatant was decanted and the was pellet resuspended in 10 ml DMEM for cell counting. $5.65\times10^7$ myeloma cells were added to the spleen cell suspension. The combined cells were centrifuged at 2000 rpm for 10 minutes. Following centrifugation, the supernatant was decanted.

1 ml PEG 1500 (1 ml) (Boehringer Mannheim Biochemicals, cat. #783-641) at room temperature was added to the pellet. The cells were very gently resuspended with a 2 ml pipet and an automatic pipettor. The cell suspension was diluted very slowly by the addition of 10 ml DMEM dropwise over 10 minutes with the gentle swirling of the tube to keep the cells in suspension. The suspension was then slowly diluted to 45 ml with DMEM and centrifuged I0 minutes at 1500 rpm. The supernatant was decanted, the pellet washed gently with 10 ml DMEM and recentrifuged at 1500 rpm for 10 minutes. Following the fused cell washes, the cells were resuspended in prewarmed HAT medium containing 5% Origin-HCF (#IG-50-0615 Fisher Scientific), and two drops of the suspension were placed in 60 wells each of Primaria Microtest III plates (Falcon #3870) leaving the outer row of wells empty. The outer wells were given 200 μl each of DMEM containing penicillin/streptomycin, and plates were placed in a $CO_2$ incubator.

Cells were refed after 7 days with HAT/5% Origen-HCF medium. Clusters of hybridomas begin to appear after 5-7 days. Further feedings were made without amingstern or Origen-HCF.

6.3. Screening For Hybridomas

Sen1-001 mycelial extract was diluted to 5 μg/ml in carbonate buffer (1.59 g/l $Na_2CO_3$, 2.93 g/l $NaH_2CO_3$, pH 9.6) and 360 μl was placed in each well of a microtiter plate (Nunc #468667). After a 3 hour room temperature incubation, the plates were washed 3 times with carbonate buffer. Remaining binding sites on the wells were blocked by adding 400 μl per well of nonfat dry milk solution. After 30 minutes, the nonfat dry milk solution was shaken out of the plates, the plates are blotted on paper towels and dried overnight in a 37° C. convection incubator (Precision, Model 4EM, #31574). 100 μl of supernatant was placed in each well and incubated 10 minutes on a plate shaker (Flow, #541305). The remaining solution was discarded and the plates were washed 5 times with wash buffer (24.2 g/l Tris, 87.7 g/l NaCl, 0.1 g/l Thimerosal, 50 g/l Tween-80, pH 7.87). 100 μl of KPL Peroxidase conjugate Goat Anti-Mouse IgG (diluted 1:1000 in 0.1% BSA-PBS (1 μg/l BSA, 2.18 g/l $NaH_2PO_4$, 0.56 g/l $NaH_2PO_4$, 8.76 g/l NaCl, pH 7.2) was then added to each well and incubated 10 minutes on the shaker. The remaining solution was discarded and the plates were washed 5 times with wash buffer. 100 μl ABTS substrate (23 g/l Citric Acid, 0.5 ml/l 30% $H_2O_2$, pH 4.0; 15 mg/ml ABTS; ABTS concentrate is diluted 1:25 in the citric acid buffer) was placed into each well and incubated 10 minutes on the shaker. The reaction was stopped by adding 50 μl per well of 1.5% NaF. Absorbance was read at 405 nm.

A number of hybridomas were found to secrete antibodies which reacted with *Leptosphaeria nodorum*. A single antibody screen was conducted with an expanded panel of *L. nodorum* isolates to determine the reactivity of the antibodies with a broad range of different isolates. These results are shown on Table 1.

TABLE 1

Single antibody indirect ELISA screen of six monoclonal antibodies made against *Leptosphaeria nodorum* against isolates of *L. nodorum*.

| | MONOCLONALS AGAINST *Leptosphaeria (Septoria) nodorum* | | | | | |
|---|---|---|---|---|---|---|
| Isolate | 8C7 | 5C6 | 11E3 | 6F3 | 5C3 | 7E9 |
| Mean | 0.503 | 0.578 | 0.263 | 0.413 | 0.237 | 0.455 |
| Sen 1 | 0.426 | 0.575 | 0.150 | 0.194 | 0.085 | 0.233 |
| Sen 2 | 0.527 | 0.193 | 0.355 | 0.239 | 0.108 | 0.255 |
| Sen 4 | 0.350 | 0.702 | 0.452 | 0.223 | 0.128 | 0.266 |
| Sen 6 | 0.087 | 0.086 | 0.070 | 0.182 | 0.029 | 0.059 |
| Sen 7 | 0.179 | 0.233 | 0.411 | 0.839 | 0.019 | 0.072 |
| Sen 8 | 0.738 | 0.979 | 0.627 | 0.804 | 0.214 | 0.404 |
| Sen 9 | 0.888 | 1.264 | 0.726 | 0.377 | 0.571 | 0.836 |
| Sen 10 | 0.391 | 0.349 | 0.619 | 0.368 | 0.192 | 0.361 |
| Sen 11 | 1.396 | 2.000 | 0.499 | 0.582 | 0.536 | 0.873 |
| Sen 14 | 0.037 | 0.025 | 0.017 | 0.295 | 0.013 | 0.023 |
| Sen 16 | 0.000 | 0.000 | 0.080 | 0.423 | 0.000 | 0.000 |
| Sen 17 | 0.044 | 0.073 | 0.041 | 0.212 | 0.037 | 0.044 |
| Sen 31 | 0.339 | 0.291 | 0.104 | 0.250 | 0.119 | 0.496 |
| Sen 32 | 0.348 | 0.591 | 0.015 | 0.493 | 0.155 | 0.402 |
| Sen 33 | 0.190 | 0.118 | 0.111 | 0.473 | 0.159 | 0.171 |
| Sen 34 | 0.801 | 1.005 | 0.305 | 0.669 | 0.576 | 0.934 |
| Sen 41 | 0.456 | 0.451 | 0.052 | 0.327 | 0.225 | 0.541 |
| Sen 42 | 0.430 | 0.544 | 0.066 | 0.423 | 0.243 | 0.548 |
| Sen 44 | 0.433 | 0.768 | 0.293 | 0.893 | 0.267 | 0.580 |
| Sen 45 | 2.000 | 1.310 | 0.275 | 0.000 | 1.064 | 2.000 |

Using a double antibody sandwich ELISA assay, suitable antibodies were selected for cross-reactivity screens against selected pathogen extracts. Microwells were sensitized using monoclonal antibody at 5 μg/ml in carbonate buffer, 100 μl per well as the capture antibody. The blocking procedure was performed as described supra. The binding of the monoclonal antibody to the pathogen extracts was detected using sheep anti-Sen-HP (horseradish peroxidase) conjugate. These results are presented in Table 2.

TABLE 2

Early cross-reactivity screening against selected pathogen extracts.

| | Pathogen Extract[a] | | | | | | | | |
|---|---|---|---|---|---|---|---|---|---|
| Antibody | Set3 | Set3G | Set4 | Set4G | Senl | Ptrl | Mfl | Unsen-sitized | Class |
| Senl5C6 | 0.02 | 0.03 | 0.03 | 0.02 | 2.25+ | 0.02 | 0.01 | 0.01 | IgG2a |
| Senl7E9 | 0.00 | 0.01 | 0.02 | 0.00 | 0.34 | 0.01 | 0.00 | 0.01 | $IgG_1$ |
| Senl8C7 | 0.03 | 0.05 | 0.06 | 0.04 | 0.45 | 0.03 | 0.01 | 0.00 | $IgG_1$ |

[a]Abbreviations: Set = *Septoria tritici*; Sen = *S. norodum*; Ptr = *Pyrenophora tritici repentis*; Mf = *Mycosphaerella fijiensis*

Selected monoclonal antibody supernatants were tested against an extended panel of related and unrelated fungal isolates in an indirect ELISA. The isolate extracts were bound to microtiter plates at 5 μg/ml. The results of this screen are presented in Table 3.

TABLE 3

Screening by indirect ELISA of *Leptosphaeria (Septoria) nodorum* monoclonal antibody supernatants against an extended panel of related and unrelated fungal isolates.

| | | MEAN ABSORBANCE (405 nm) +/− STANDARD DEVIATION | | |
|---|---|---|---|---|
| SPECIES | ISOLATES | Senl5C6 | Senl8C7-1 | Senl1E3 |
| *Septoria nodorum* | 9 | 0.71 +/− 0.62 | 0.54 +/− 0.40 | 0.43 +/− 0.22 |
| Alternaria spp. | 2 | 0.02 +/− 0.0 | 0.01 +/− 0.01 | 0.01 +/− 0.02 |
| Aspergillus spp. | 4 | 0.02 +/− 0.01 | 0.01 +/− 0.0 | 0.0 |
| Bipolaris spp. | 5 | 0.01 +/− 0.02 | 0.01 +/− 0.01 | 0.0 |
| Botrytis spp. | 3 | 0.02 +/− 0.01 | 0.01 +/− 0.01 | 0.0 |
| *Choridium musae* | 1 | 0.03 | 0.0 | 0.0 |
| Cladosporium spp. | 2 | 0.02 +/− 0.02 | 0.0 | 0.01 +/− 0.01 |
| *Colletotrichum graminicola* | 2 | 0.00 +/− 0.00 | 0.00 +/− 0.00 | 0.01 +/− 0.01 |
| *Curvularia lunata* | 1 | 0.02 | 0.0 | 0.0 |
| *Diplodia gossypina* | 1 | 0.0 | 0.0 | 0.0 |

TABLE 3-continued

Screening by indirect ELISA of *Leptosphaeria (Septoria) nodorum* monoclonal antibody supernatants against an extended panel of related and unrelated fungal isolates.

| SPECIES | ISOLATES | MEAN ABSORBANCE (405 nm) +/− STANDARD DEVIATION | | |
|---|---|---|---|---|
| | | Sen15C6 | Sen18C7-1 | Sen11E3 |
| Drechslera spp. | 2 | 0.0 | 0.0 +/− 0.0 | 0.0 |
| Epicoccum nigrum | 1 | 0.03 | 0.02 | 0.01 |
| Fusarium spp. | 4 | 0.0 | 0.0 | 0.02 +/− 0.03 |
| Helminthosporium sativum | 4 | 0.03 +/− 0.03 | 0.02 +/− 0.04 | 0.03 +/− 0.04 |
| Lambertella sp. | 1 | 0.00 | 0.03 | 0.0 |
| Lanzia luteo-virescens | 1 | 0.05 | 0.0 | 0.0 |
| Leptosphaeria korrae | 3 | 0.023 +/− 0.03 | 0.01 +/− 0.01 | 0.01 +/− 0.01 |
| Monilia spp. | 2 | 0.02 +/− 0.00 | 0.0 | 0.0 |
| Mortierella spp. | 2 | 0.03 +/− 0.02 | 0.01 +/− 0.00 | 0.0 |
| Myriosclerotinia dennisii | 1 | 0.0 | 0.0 | 0.0 |
| Penicillium spp. | 4 | 0 03 +/− 0.03 | 0.01 +/− 0.01 | 0.0 |
| Phialophora graminicola | 1 | 0.0 | 0.0 | 0.0 |
| Pseudocercosporella herpotrichoides | 1 | 0.01 | 0.0 | 0.0 |
| Pyrenophora tritici-repentis | 3 | 0.03 +/− 0.01 | 0.01 +/− 0.01 | 0.07 +/− 0.10 |
| Pythium spp. | 10 | 0.02 +/− 0.02 | 0.01 +/− 0.01 | 0.0 |
| Rhizoctonia spp. | 10 | 0.01 +/− 0.01 | 0.0 | 0.0 |
| Rhizopus stolonifer | 2 | 0.0 | 0.01 +/− 0.01 | 0.0 |
| Sclerotium spp. | 3 | 0.01 +/− 0.01 | 0.0 | 0.01 +/− 0.01 |
| Septoria tritici | 3 | 0.01 +/− 0.02 | 0.0 | 0.01 +/− 0.01 |
| Stemphylium vesicarium | 2 | 0.0 | 0.0 | 0.0 |

After several screens, the antibody Sen15C6 was selected on the basis of its performance in a double antibody sandwich assay. Sen15C6 was purified from supernatant using Protein A affinity chromatography. Microwells were sensitized using antibody at 5 μg/ml in carbonate buffer, 100 μl per well. The assay was conducted against *Leptosphaeria nodorum* antigen extract, *L. nodorum* infected wheat leaf material, healthy wheat leaf and buffer control. The results of the double antibody assay are presented in Table 4. Sheep anti-*S. nodorum*-horseradish peroxidase conjugate was used as the tagged antibody.

TABLE 4

| ANTIGEN | MONOCLONAL ANTIBODY | | |
|---|---|---|---|
| | Sen15C6 | Sen17E9 | Sen18C7 |
| Sen1-001 | | | |
| 10 μg/ml | 2.00+ | 2.00+ | 2.00+ |
| 1 μg/ml | 0.638 | 0.637 | 0.355 |
| 0.5 μg/ml | 0.179 | 0.303 | 0.169 |
| Sen1 infected leaf | | | |
| 1:1* | 1.489 | 0.576 | 0.332 |
| 1:10* | 0.349 | 0.298 | 0.208 |

TABLE 4-continued

| ANTIGEN | MONOCLONAL ANTIBODY | | |
|---|---|---|---|
| | Sen15C6 | Sen17E9 | Sen18C7 |
| 1:100* | 0.147 | 0.268 | 0.152 |
| Healthy Leaf undiluted | 0.102 | 0.243 | 0.179 |

*dilution of infected wheat leaves in a solution of 0.1% BSA in PBS buffer.

These results indicate that the Sen15C6 antibody may be used in immunoassays to detect *Leptosphaeria nodorum* in antigen extract as well as in infected leaves.

6.4. "Leptosphaeria Korrae" Monoclonal

Workers at Ohio State University have previously reported production of monoclonal antibodies to *Leptosphaeria korrae* (Shane, W. W. and S. T. Nameth, 1988, Phytopathology 78:1521 (Abst)). This antibody (provided by Dr. William Shane) was tested in an indirect ELISA to determine cross-reactivity against a panel consisting of three isolates of *L. korrae* and 21 isolates of other Leptosphaeria-related and non-related fungi. These results are shown in Table 5.

TABLE 5

Screening of cross-reactivity in an indirect ELISA of a 1/16 dilution of supernatant of *Leptosphaeria korrae* monoclonal antibody (LKc50) against Leptosphaeria-related and non-related fungi.

| Isolate | Isolate Code | Number of isolates tested | Net Absorbance[a] (405 nm) |
|---|---|---|---|
| Leptosphaeria korrae | Lk3, Lk6 and Lk5 | 3 | 2.000+ |
| Alternaria sp. | Alsp2 | 1 | 1.562 |
| Botrytis cinerea | Bc2 | 1 | 0.087 |
| Bipolaris sorokiniana | Bs2 | 1 | 0.045 |
| Curvularia lunata | Cu11 | 1 | 0.135 |
| Drechslera gigantea | Dg1 | 1 | 0.041 |
| Epicoccum nigrum | En1 | 1 | 2.000+ |
| Epicoccum sp. | Esp1 | 1 | 1.494 |
| Helminthosporium sativum | Hs3 | 1 | 0.093 |
| Mortierella epigama | Me1 | 1 | 0.296 |
| Pythium aphanidermatum | Pa1 and Pa15 | 2 | 0.466 |
| Pythium graminicola | Pg2 | 1 | 0.183 |
| Pythium irregulare | Pi1 | 1 | 0.107 |
| Pythium myriotylum | Pmy2 | 1 | 0.217 |
| Pythium torulosum | Pt3 | 1 | 0.071 |

TABLE 5-continued

Screening of cross-reactivity in an indirect ELISA of a 1/16 dilution of supernatant of *Leptosphaeria korrae* monoclonal antibody (LKc50) against Leptosphaeria-related and non-related fungi.

| Isolate | Isolate Code | Number of isolates tested | Net Absorbance[a] (405 nm) |
|---|---|---|---|
| *Pythium ultimum* | Pu7 | 1 | 0.124 |
| *Septoria nodorum* | Sen1 and Sen2 | 2 | 0.059 |
| *Septoria nodorum* | Sen3 | 1 | 1.518 |
| *Stemphylium vesicarium* | Stv1 and Stv2 | 2 | 0.368 |

[a]Net absorbance reading = Absorbance value of sample-absorbance value of Buffer A The results clearly show that the other known monoclonal antibody to a species of Leptosphaeria is strongly cross-reactive with fungi outside the genus Leptosphaeria. Such cross-reactivity is particularly disadvantageous with fungi of the genus Epicoccum. The latter is a common saprophyte of turfgrass and could cause problems if turfgrass with advanced symptoms were inadvertently sampled. Thus, this antibody may be unsuitable for diagnostic purposes.

6.5. On Site Assays

The on-site assays were performed on single leaves using abrasive pads for grinding which were put into bottles containing 2 ml of extraction buffer and after shaking, filtered through a 0.02 μ filter. Six drops of the filtered extract were put on an absorptive device coated with the captive antibody. After sequentially adding two drops each of the enzyme-tagged antibody, a rinse solution and an enzyme substrate, the test circle turned blue when the fungal antigen was present in the sample. The addition of two drops of a finishing solution stopped the color reaction. The amount of antigen present may be measured by measuring the relative reflectance present in X-Rite units using an X-Rite meter and/or Agrimeter.

A sensitivity comparison was made between the rapid (on-site) assay and multi-well assay for dilutions of Sen1 antigen in healthy wheat extract.

The performance of the On-Site assays was also evaluated using field wheat infected with *S. nodorum* (Tables 6 and 7). The wheat varieties used, Twain and Traveler, were naturally infected with *S. nodorum* in test plots. The three lower-most leaves (plants still in the tillering stage) from each of six plants were removed and extracted individually using two Extrak pads/2 ml Buffer Z-5. The extracts filtered through 0.02 Anotop ® filter and assayed in the 1990 *S. nodorum* and *S. tritici* multiwell kits. The samples that reacted strongly in the *S. nodorum* multiwell kits were also assayed in the On-Site kit.

No plant sample matrix effects were observed for the On-Site assays, and X-Rite meter readings ranged from 31 to 86 for samples that gave off-scale readings in the multiwell assay.

TABLE 6

Assays of *Septoria nodorum*-infected wheat (c.v. Twain) in the 1990 *S. nodorum* multiwell kits and the 1990 *S. nodorum* on-site kit.

| Sample | Leaf # | % Necrosis | +/− pycnidia | S. nodorum Absorbance 405 nm | S. nodorum X-Rite Reading |
|---|---|---|---|---|---|
| Twain 1 | 1 | 40 | + | 2.0+ | 53 |
|  | 2 | 0-1 | − | 0.00 | — |
|  | 3 | 0 | − | 0.00 | — |
| Twain 2 | 1 | 50 | + | 2.0+ | 40 |
|  | 2 | 0-1 | − | 0.00 | — |
|  | 3 | 0 | − | 0.19 | — |
| Twain 3 | 1 | 30 | + | 2.0+ | 56 |
|  | 2 | 0-1 | − | 0.00 | — |
|  | 3 | 0 | − | 0.00 | — |
| Twain 4 | 1 | 40 | + | 2.0+ | 45 |
|  | 2 | 0-1 | − | 0.00 | — |
|  | 3 | 0 | − | 0.00 | — |
| Twain 5 | 1 | 20 | + | 1.64 | 25 |
|  | 2 | 0-1 | − | 0.34 | 8 |
|  | 3 | 0 | − | 0.18 | — |
| Twain 6 | 1 | 30 | + | 2.0+ | 46 |
|  | 2 | 0 | − | 0.00 | — |
|  | 3 | 0 | − | 0.00 | — |

Leaves were numbered 1-3 starting from the bottom of the plant and counting upward. Net MW absorbances were calculated using the formula (Sample abs. 405 nm − Buffer Z-5 abs. 405 nm). Buffer Z-5 yielded an absorbance of 0.332 in the *S. nodorum* kit. Positive control absorbances for *S. nodorum* was 0.829. Plants at the time of the assays were approximately at growth stage #24.
— = Not tested

TABLE 7

Assays of *Septoria nodorum*-infected wheat (c.v. Traveler) in the 1990 *S. nodorum* and the 1990 *S. nodorum* on-site kit.

| Sample | Leaf # | % Necrosis | +/− pycnidia | S. nodorum Absorbance 405 nm | S. nodorum X-Rite Reading |
|---|---|---|---|---|---|
| Traveler 1 | 1 | 50 | + | 2.0+ | 86 |
|  | 2 | 10 | − | 0.51 | — |
|  | 3 | 0 | − | 0.13 | — |
| Traveler 2 | 1 | 30 | + | 2.0+ | 48 |
|  | 2 | 0-1 | − | 0.17 | — |
|  | 3 | 0 | − | 0.00 | — |
| Traveler 3 | 1 | 30 | + | 2.0+ | 55 |
|  | 2 | 0 | − | 0.00 | — |
|  | 3 | 0 | − | 0.00 | — |
| Traveler 4 | 1 | 50 | + | 2.0+ | 68 |
|  | 2 | 0-1 | − | 0.20 | — |
|  | 3 | 0 | − | 0.24 | — |
| Traveler 5 | 1 | 30 | + | 2.0+ | 65 |
|  | 2 | 5 | − | 0.24 | — |
|  | 3 | 0-5 | − | 0.04 | — |
| Traveler 6 | 1 | 25 | + | 2.0+ | 31 |
|  | 2 | 0 | − | 0.00 | — |
|  | 3 | 0 | − | 0.00 | — |
| Healthy 1 (ND495) | 1 | 0 | − | 0.00 | 1 |
|  | 2 | 0 | − | 0.00 | 0 |
|  | 3 | 0 | − | 0.00 | 8 |

Leaves were numbered 1-3 starting from the bottom of the plant and counting upward. Net MW absorbances were calculated using the formula (Sample abs. 405 nm − Buffer Z-5 abs. 405 nm). Buffer Z-5 yielded an absorbance of 0.332 in the *S. nodorum* kit. Positive control absorbances for *S. nodorum* was 0.829. Plants at the time of the assays were approximately at growth stage #24.
— = Not tested These results indicate that the *S. nodorum* antigen may be detected using both multiwell plates and an on-site kit. Therefore, *S. nodorum* may easily be detected in the field.

7. DEPOSIT OF MICROORGANISMS

The hybridoma Sen15C6 was deposited with the American Type Culture Collection, Rockville, Md., on Aug. 1, 1989 and has been assigned the listed accession number HB 10185.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What we claim is:

1. A hybridoma that produces a monoclonal antibody which reacts specifically with *Leptosphaeria nodorum*, but which does not react with other Leptosphaeria species, or species outside the genus, wherein said hybridoma has all the identifying characteristics of HB ATCC 10185.

2. A monoclonal antibody produced by a hybridoma of claim 1.

3. A method of detecting the presence of *Leptosphaeria nodorum* in a sample suspected of containing Leptosphaeria antigens, which comprises contacting the sample with a first antibody which is a monoclonal antibody of claim 2, and observing whether an antibody-antigen reaction occurs as an indication of the presence of Leptosphaeria in the sample.

4. A method of claim 3, further comprising contacting the sample with a second antibody which reacts specifically with *Leptosphaeria nodorum*, wherein one of the antibodies is immobilized and the other is labeled with a reporter molecule.

5. A method of claim 4, wherein the second antibody is polyclonal.

6. A diagnostic kit, comprising an antibody bound to a solid support and an antibody labeled with a reporter molecular, wherein said antibodies are each capable of reacting with *Leptosphaeria nodorum*, also wherein at least one of said antibodies is a monoclonal antibody of claim 2.

7. A diagnostic kit of claim 6, wherein one antibody is polyclonal.

* * * * *